(12) United States Patent
Byrd et al.

(10) Patent No.: US 6,633,328 B1
(45) Date of Patent: Oct. 14, 2003

(54) SURGICAL LIGHTING SYSTEM WITH INTEGRATED DIGITAL VIDEO CAMERA

(75) Inventors: Robert Joe Byrd, Marbury, AL (US); Viroon Mai Ujjin, Montgomery, AL (US); Saysana Say Kongchan, Montgomery, AL (US); Howard D. Reed, Warsaw, IN (US)

(73) Assignee: Steris Corporation, Mentor, OH (US)

( * ) Notice: Subject to any disclaimer, the term of this patent is extended or adjusted under 35 U.S.C. 154(b) by 0 days.

(21) Appl. No.: 09/225,880

(22) Filed: Jan. 5, 1999

(51) Int. Cl.$^7$ .............................. H04N 9/47; A61B 1/06; F21S 33/00
(52) U.S. Cl. ..................... 348/143; 348/77; 600/249; 362/233
(58) Field of Search ............................ 348/77, 68, 42, 348/45, 143, 148, 39, 66, 61, 169, 373; 600/109, 112, 160, 249; 364/804; 362/233; 382/293

(56) References Cited

U.S. PATENT DOCUMENTS

| | | | |
|---|---|---|---|
| 3,919,475 A | | 11/1975 | Dukich et al. |
| 4,051,534 A | | 9/1977 | Dukich et al. |
| 4,395,731 A | * | 7/1983 | Schoolman .................. 348/143 |
| 4,517,963 A | * | 5/1985 | Michel ........................ 600/126 |
| 4,727,416 A | | 2/1988 | Cooper et al. |
| 4,797,736 A | | 1/1989 | Kloots et al. |
| 5,016,098 A | | 5/1991 | Cooper et al. |
| 5,115,307 A | | 5/1992 | Cooper et al. |
| 5,251,025 A | | 10/1993 | Cooper et al. |
| 5,290,168 A | | 3/1994 | Cooper et al. |
| 5,313,306 A | * | 5/1994 | Kuban et al. ................. 348/39 |
| 5,347,431 A | * | 9/1994 | Blackwell et al. ........... 362/233 |
| 5,429,502 A | | 7/1995 | Cooper et al. |
| 5,803,905 A | * | 9/1998 | Allred et al. ................ 600/249 |
| 6,041,860 A | * | 3/2000 | Nazzal et al. .......... 166/250.01 |

FOREIGN PATENT DOCUMENTS

DE 196 53 507 A1 6/1998

OTHER PUBLICATIONS

Berchtold: ChromoVision Surgical Camera System sales brochure.

* cited by examiner

*Primary Examiner*—Gims S. Philippe
(74) *Attorney, Agent, or Firm*—Fay, Sharpe, Fagan, Minnich & McKee, LLP (57) ABSTRACT

A surgical video system 10 captures an image of a surgical procedure and displays the image on a video monitor 24 remote from the surgical procedure. The system includes at least one surgical lighthead 12, a video monitor 24, and a digital video camera 22 integrated into the surgical lighthead. The digital video camera forms part of a modular digital video camera unit 20 that is conveniently removable from the surgical lighthead so that camera units having different functionalities and capabilities can be selectively substituted as needed. A control unit 26 is operatively connected to the video camera and generates command signals that are executed by the modular camera unit to rotate the image of the surgical procedure displayed on the video monitor by at least 360° and to effect image zoom operations. The control unit is responsive to input signals from multiple sources including a hand-held IR/RF remote transmitter module 38, a wall mounted keypad 30, and a footswitch 40. Associated with the control unit and the video monitor, a recorder 42 is provided for archival of video image data.

20 Claims, 8 Drawing Sheets

SURGICAL LIGHTING SYSTEM WITH INTEGRATED DIGITAL VIDEO CAMERA

BACKGROUND OF THE INVENTION

The present invention is directed to the art of surgical videography and, more particularly, to a method and apparatus for displaying and recording live videographic images of a surgical procedure from the vantage point of a digital camera disposed within an overhead surgical lighthead. The present invention will be described with particular reference surgical videography but it should be understood that the invention has broader applications and uses such as in the theater arts, industrial processes, or anywhere there is a need for the real time display or recording of an image taken from a digital camera disposed within a lighting apparatus.

In nearly all medical surgical procedures, highly specialized apparatus are used to provide filtered light known as "cold" light. The devices are engineered to illuminate surgical fields without heating the biological material under the light. Typically, surgical lighting apparatus of this type include one or more lightheads that are suspended from a corresponding set of interconnected articulated arms for supporting the lightheads in multiple positions relative to the surgical field. One common form of surgical lighting equipment includes a ceiling mounted support system that is used to suspend a pair of substantially circular lightheads from arms that are manually movable into place as needed before or during a surgical procedure. The lightheads are normally spaced from the floor well above the heads of the surgeon and other operating room personnel and therefore offer an excellent vantage point from which to observe the medical procedure as it is being performed.

In certain surgical procedures, it is desirable to record the entire surgical session for use afterwards as a teaching tool or in defense of medical malpractice lawsuits, or the like. Another reason video cameras have been used during surgical procedures is to provide a real time monitor of the procedure to one or more shifts of surgical team members that have a need to observe the status of the procedure in advance of the point at which their respective tasks are to be performed in turn. Oftentimes, one or more remote monitors are used in separate waiting or prep rooms so that the various surgical teams can independently observe the ongoing procedure and take whatever steps are necessary to prepare themselves for their turn at the patient.

One commercial attempt to provide live videographic images of a surgical procedure as it is performed is provided by Berchtold Corporation in the form of their ChromoVision™ surgical camera system. Basically, the Berchtold offering includes a digitally processed camera that is disposed within the handle of a surgical lighthead. The lighthead supporting the camera is an otherwise standard cold light unit and, as such, is suspended from overhead by multiple pivotally connected arm segments. The distal end of each arm segment includes a fork-like member that is rotatably connected to the arm segment on one end and is connected to opposite sides of the lighthead on the other end.

In the Berchtold system described above, although the multiple pivotable support arms enable full 360° rotation of the lighthead, the camera disposed within the handle of the lighthead can only be rotated 300°. To do so, the surgeon or circulating nurse must reach overhead and manually adjust the camera by rotating the lighthead handle until the desired picture orientation is obtained. That is, the camera is only manually rotatable. Normally, the lighthead handle is sterile and, accordingly, only sterilized personnel can effect picture orientation adjustments.

In order to adjust the field of view of the digitally processed camera in the Berchtold system, a motor driven zoom lens is provided to enable video images of the surgical procedure from a wide angle or close-up range. The motorized lens is connected to a control box that receives zoom commands from either push buttons on the face of the control box or an optional foot pedal switch disposed on the floor of the surgical room adjacent the patient table.

One major disadvantage of the above video system is that the camera cannot be rotated a full 360°, as noted above. This makes it difficult to properly orient the camera to provide understandable video images. Upside down images could lead to surgeon confusion and cause accidental missteps that might injure the patient.

Another disadvantage of the prior art system described above is that the footswitch cannot be used to effect video image rotation.

Yet another disadvantage of the above prior art system is that at least two people are required to operate the system, namely, a first person to rotate the lighthead handle to properly orient the camera and a second person to operate the footswitch or control box to adjust the zoom lens of the camera.

It would therefore be desirable to provide a surgical videographic system having a surgical lighthead with an integrated digital video camera that can provide fully motorized 360° image rotation and that is easier to operate and less awkward than the system described above.

It would further be desirable to provide a fully motorized surgical video system that can be operated by fewer people than the system described above to reduce operating room overhead.

SUMMARY OF THE INVENTION

In accordance with the present invention, a surgical video system is provided for capturing an image of a surgical procedure and displaying the image on a video monitor remote from the surgical procedure. The video system includes at least one surgical lighthead adapted to generate a light beam and direct the light beam towards the surgical procedure. A video camera is integrated into the at least one surgical lighthead. The video camera generates an electronic image signal representative of the surgical procedure for display on a video monitor operatively connected to-the video camera. The video camera is adapted to modify the signal displayed on the monitor in response to a first command signal to selectively rotate the image of the surgical procedure displayed on the video monitor. Together with the surgical lighthead-and the video monitor and camera, the video system includes a control unit operatively connected to the video camera for generating the first command signal in response to an input signal from an operatively associated external source.

In accordance with an aspect of the invention, the video camera is a digital video camera adapted to generate a digital electronic image signal representative of the surgical procedure for display on the video monitor. The digital video camera is adapted to physically rotate independent of the surgical lighthead in response to the first command signal to rotate the image of the surgical procedure displayed on the video monitor.

In accordance with another aspect of the invention, the digital video camera is adapted to physically rotate at least 360° within the surgical lighthead relative to the first command signal to rotate the image of the surgical procedure displayed on the video monitor at least 360°.

In accordance with still yet another aspect of the invention, at least a one of a footswitch, a manual keypad, and a remote transmitter is in operative communication with the control unit for generating the input signal used by the control unit to generate the first command signal causing the digital video camera to rotate the image of the surgical procedure displayed on the video monitor.

Still yet further in accordance with the invention, the digital video camera is carried on a rotatable motorized frame supported within the surgical lighthead. An electric gear motor is drivingly associated with the rotatable frame. As the drive motor rotates, the frame and digital video camera carried thereon rotate as well. An electric slip ring connector electromechanically connects a first set of digital video signal wires from the digital video camera to a second set of digital video signal wires routed through the surgical lighthead toward the control unit so that rotation of the digital video camera relative to the lighthead does not cause twisting or binding of the digital video signal wires. First and second intermatable plug connectors are provided in the subject surgical video system to enable selective substitution and/or replacement of digital video camera units as modules. Each module includes an integrated collection of a rotatable frame member, an electric drive motor and a digital camera.

It is a primary object of the invention to provide a surgical video system including a digital video camera integrated into a surgical lighting system, the digital video camera being motorized to rotate at least 360° relative to the surgical lighthead in response to a first command signal.

It is another object of the invention to provide remote control of the digital video camera rotation. Remote control can be effected using a footswitch, a manual RF or IR transmitter, a wall mounted keypad or all of the above in any combination.

It is yet another object of the invention to provide remote control of the digital video camera zoom lens operation. Zoom lens remote control can be effected using the footswitch, a manual RF or IR transmitter, a wall mounted keypad or all of the above in any combination.

It is still yet another object of the invention to provide a modular camera head unit including a rotatable frame member, an electric drive motor, and a digital video camera that can be selectively replaced or substituted as needed using quick connect electrical plugs and manual thumb screws.

Still yet another object of the invention is to provide an integrated surgical lighting system with video image capabilities that provides a clear and high definition image of the surgical procedure with substantially no noise injected into the video image signal.

These and other objects, advantages, and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
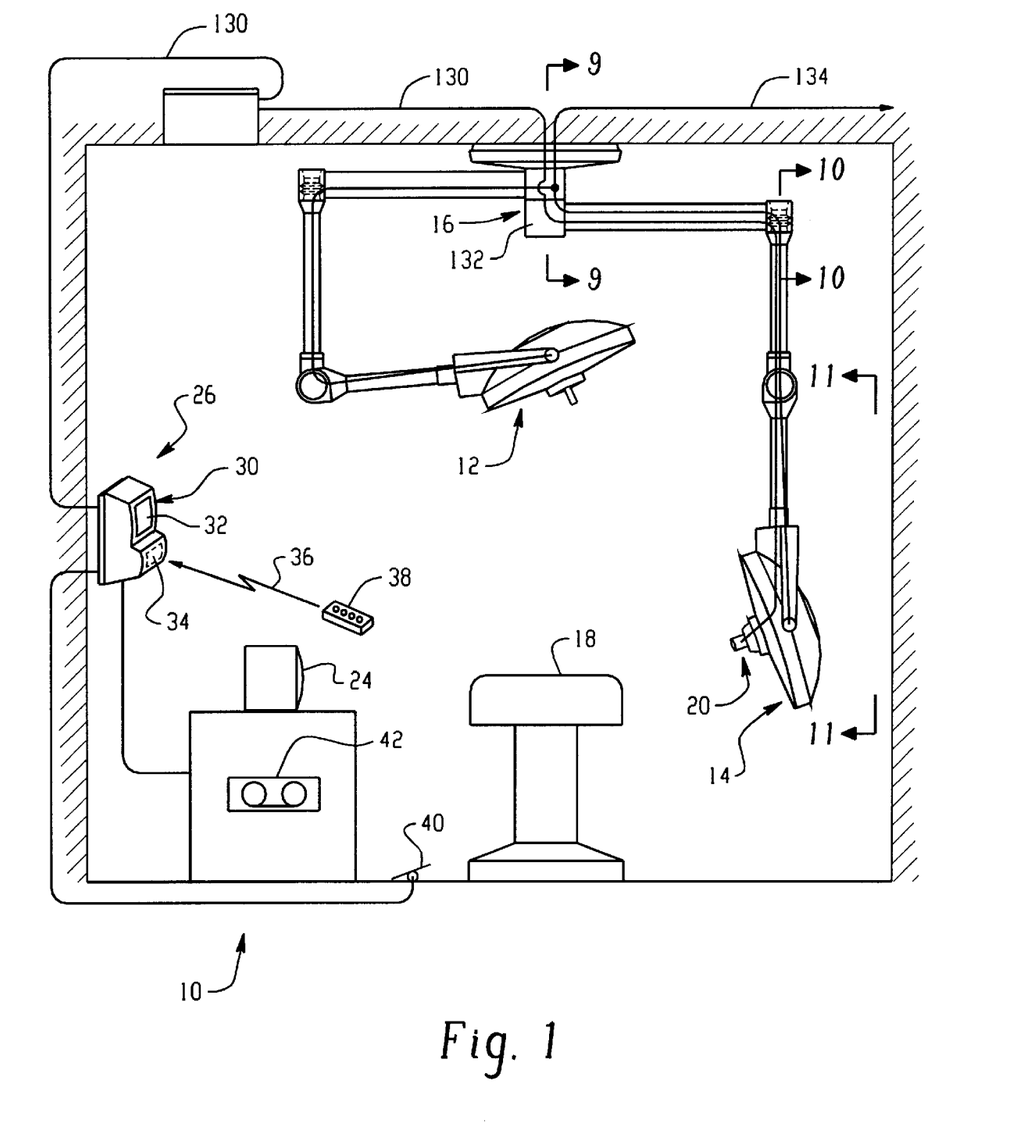
FIG. 1 is a schematic view of a surgical videographic system including a surgical lighting system with integrated digital video camera constructed in accordance with the present invention.

Referring now to the drawings wherein the showings are for the purposes of illustrating the preferred embodiment of the invention only and not for purposes of limiting same, FIG. 1 shows a surgical video system 10 formed in accordance with the present invention. As shown, the system includes upper and lower surgical lightheads 12, 14 suspended from overhead by a standard multi-segment surgical lighting support system 16. The support system is movable into a range of positions and orientations to direct the columns of light falling from the first and second surgical lightheads onto the surgical field as needed.

Figure 2:
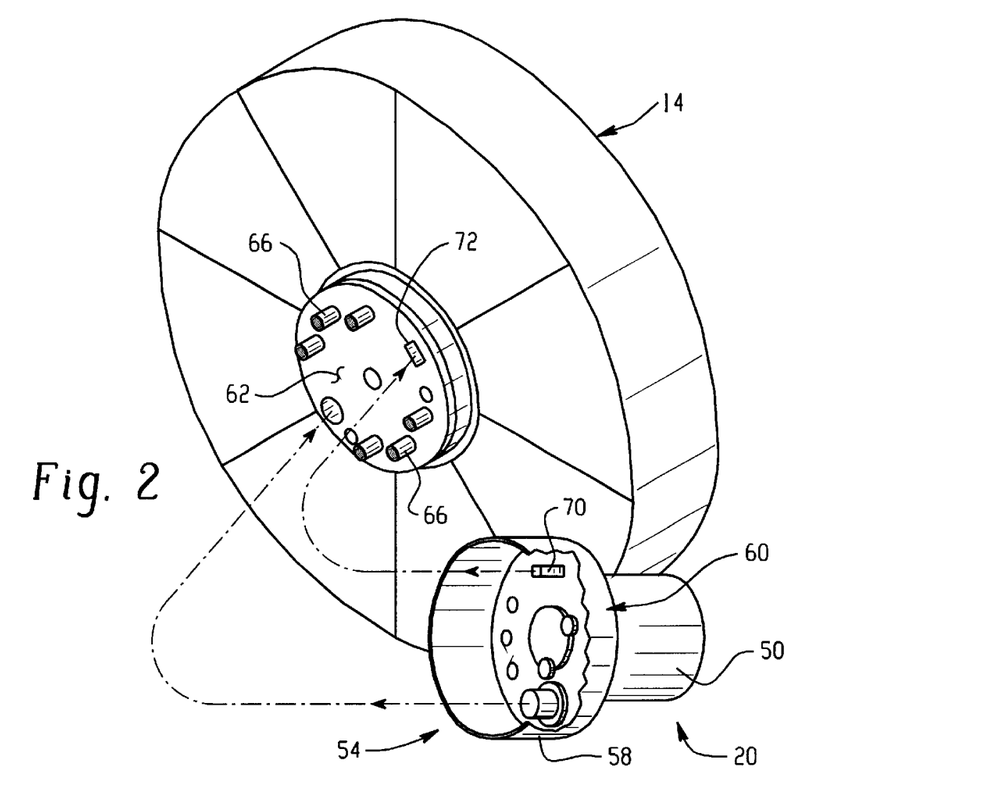
FIG. 2 is a schematic perspective view of a modular digital video camera unit of the present invention shown separated from the overall lighting system illustrated in FIG. 1.

Of particular importance to the present invention, the lower surgical lighthead 14 carries a modular digital video camera unit 20 at the center of the lighthead as shown. The video camera unit has the general outward appearance of a standard surgical lighthead handle and, in accordance with the invention, is used to manually manipulate the lower surgical lighthead 14 into operative position relative to the surgical field 18 as needed. Preferably, the modular video camera unit is selectively removable (FIG. 2) and can be replaced with other modules having different functions or capabilities as will be described in greater detail below.

In order to provide remote images of surgical procedures performed adjacent the surgical lightheads, the surgical video system 10 of the present invention includes a video camera 22 (FIGS. 5–8) disposed within the modular video camera unit 20. In that way, the video camera 22 is integrated into the lower surgical lighthead 14 in an unobtrusive manner.

Functionally, the video camera generates an electronic image signal representative of the surgical procedure performed within the field of view of the camera adjacent the surgical lighthead. The electronic image signal is used by a video monitor 24 disposed nearby to display images of the-surgical procedure in real time.

The video monitor 24 is interfaced to the digital video camera 22 by a control unit 26 that is preferably arranged within the operating room on a wall or the like and spaced apart from the surgical field 18. The control unit 26 is operatively electrically connected to the video camera 22 within the camera unit 20 to generate the command signals used by the camera to perform video image rotation functions and lens zoom adjustments.

The control unit 26 is shown with a manual keypad 30 having a series of individual programming keys 32 for manually entering commands into the surgical video system. The manual commands also include video image rotation functions and lens zoom adjustments.

The control unit further includes a remote signal receiving sensor 34 adapted to receive remote signals 36 carried through the air and generated by a remote transmitter module 38. The signals are preferably radio frequency (RF) signals but infrared (IR) signals could be used as well. Preferably, the remote transmitter module 38 includes a set of programming keys similar to or comprising a subset of the programming keys that are carried on the manual keypad 30. The control unit includes a processor connected to the signal receiving sensor 34 for interpreting the commands generated at the remote transmitter module 38. Preferably in accordance with the present invention, the commands generated at the remote transmitter module mimic those that would normally originate from the manual keypad 30 on the control unit 26. In that way, surgical room personnel can equivalently engage the surgical video system with zoom, rotate, and focus commands using either the remote transmitter module from anywhere within the operating room or from the keypad 30 on the wall. The command signals preferably include but are not limited to video image rotate left/right, lens zoom in/out, auto/manual focus, video on/off, record on/off, and the like.

In addition to the keypad and remote transmitter module discussed above, the control unit 26 is responsive to input signals generated from a footswitch 40. According to the invention, the footswitch includes a pair of normally closed contacts that are used to generate a zoom command signal and a video image rotate signal, respectively. The pair of signals are interpreted by the control unit 26 which in turn is operative to send the appropriate command signals to the modular digital video camera unit 20 disposed on the lower surgical lighthead 14.

Lastly in connection with FIG. 1, a video image recorder 42 is provided for archiving live video images as they are displayed on the video monitor 24. Preferably, the recorder 42 is a standard 8 mm audio-video recording device, however, other tape standards or recording technologies can be used as well. Video tapes of surgical procedures can be useful to educate students on certain techniques, procedures, practices, or the like. Another use for generating archival video tapes of medical procedures is in defense of potential medical malpractice lawsuits.

Figure 3:
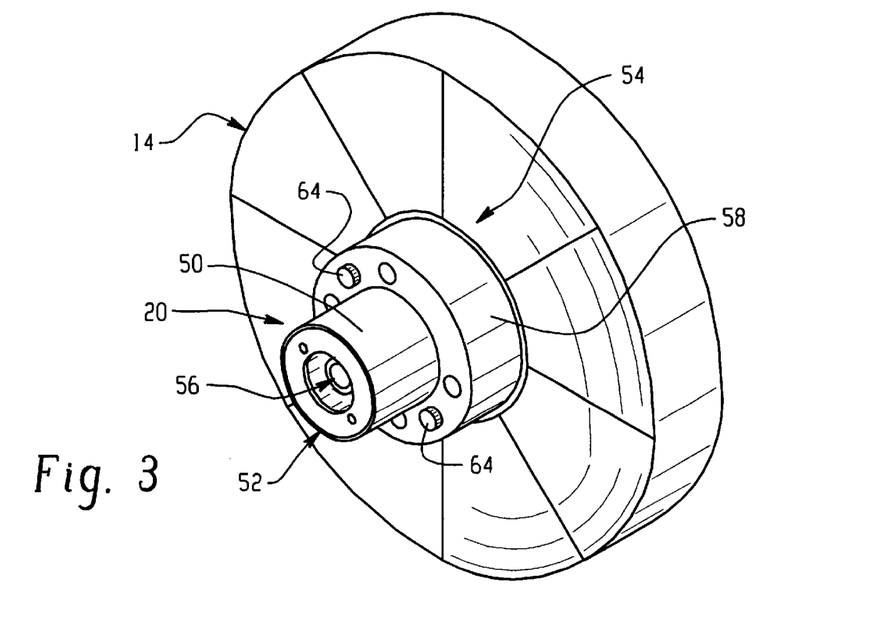
FIG. 3 is a schematic perspective view of the modular digital video camera unit of FIG. 2 shown attached to the surgical lighthead.
Figure 4:
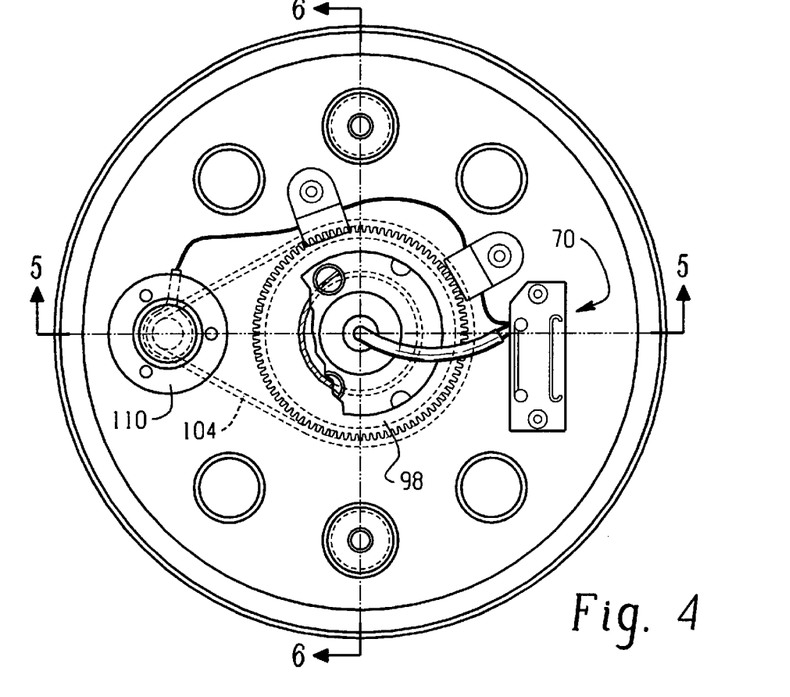
FIG. 4 is a top plan view of the modular digital video camera unit shown in FIGS. 2 and 3.
Figure 5:
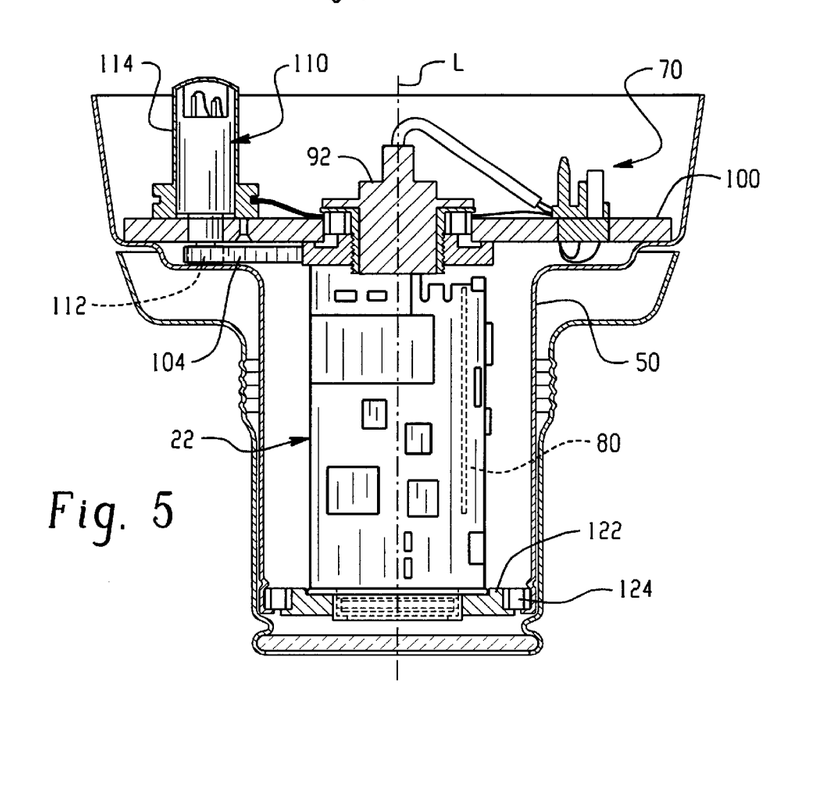
FIG. 5 is a cross sectional view of the modular digital video camera unit taken along 5—5 of FIG. 4.
Figure 6:
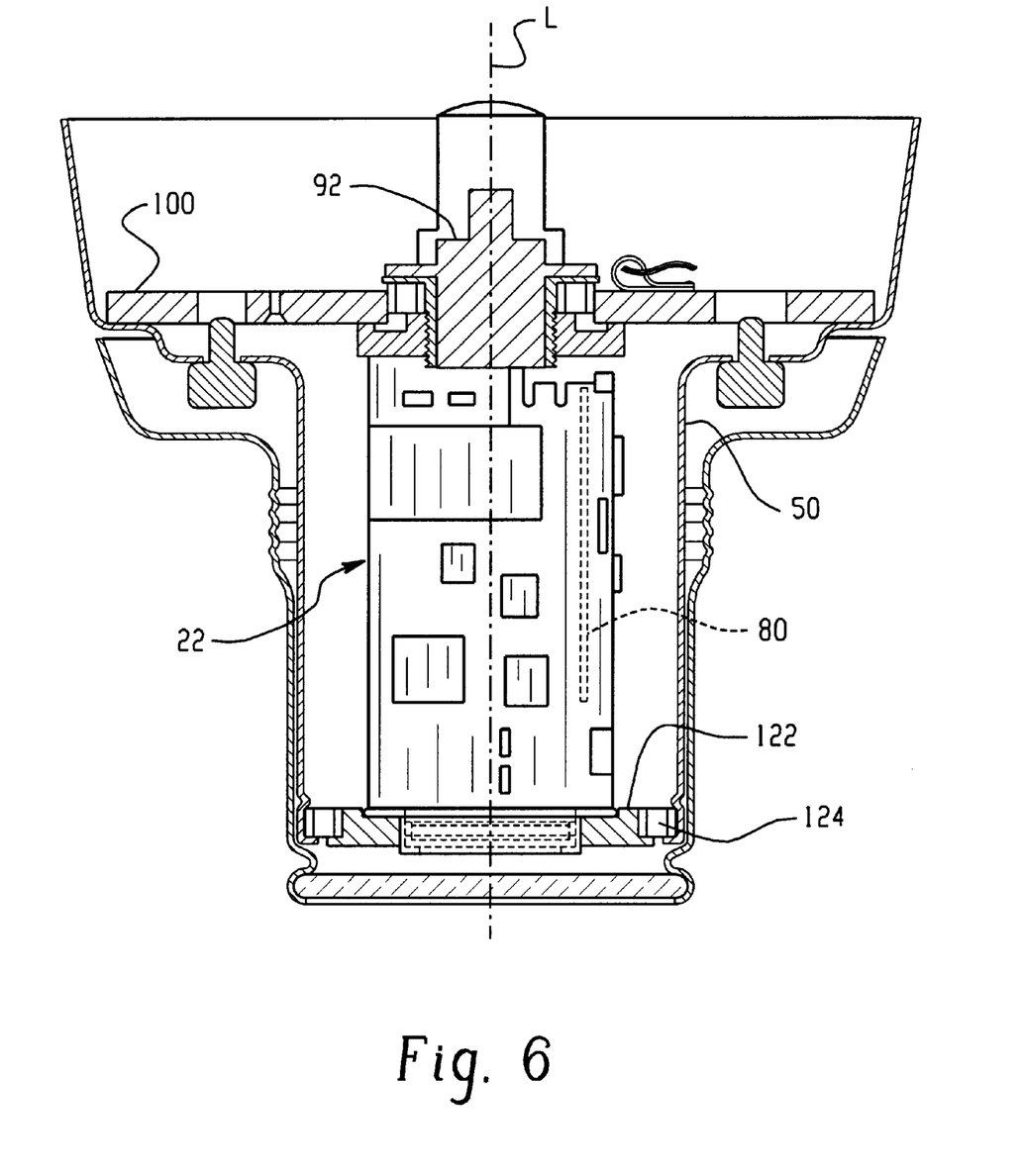
FIG. 6 is a cross sectional view of the modular digital video camera unit taken along line 6—6 of FIG. 4.

Turning now more particularly to the camera of the subject video system, an interface between the lower surgical lighthead 14 and the modular digital video camera unit 20 enables the camera unit to be easily manually removed from the lighthead and replaced with other camera units having similar size but with different functionalities or capabilities. As shown best in FIGS. 2 and 3, the video camera unit 20 includes a substantially cylindrically shaped outer shell or housing 50 having a camera lens end 52 and a mounting side 54. The camera lens end 52 includes a central aperture 56 to enable the video camera within the housing to be exposed to the surgical field. The mounting side 54 includes a circular wall member 58 that extends completely around a circular base portion 60. As shown, the base portion is substantially planar and adapted to engage a corresponding substantially planar surface 62 on the surgical lighthead 14. In the position illustrated in FIG. 3, the base portion of the camera unit and the planar surface of the lighthead are in intimate contact to provide a sound and stable support foundation for the modular digital video camera unit 20.

A set of manual thumb screws 64 are used to fasten the modular camera unit 20 to the surgical lighthead 14. Preferably, the thumb screws are captively mounted to the video camera unit so that they are not lost or mishandled during maintenance or replacement of the modular camera unit. A set of threaded holes 66 are provided in the planar surface 62 of the surgical lighthead 14 at locations and in numbers that correspond to the locations and numbers of the thumb screws 64. Preferably, the thumb screws have a knurled head so that they can be easily manually threaded into the holes 66 to securely fasten the modular camera unit to the surgical lighthead.

First and second intermatable electrical connectors 70, 72 are respectively provided on the modular digital video camera unit 20 and the surgical lighthead 14 as shown. The electrical connectors are arranged on the base portion of the camera unit 60 and the planar surface 62 of the lighthead at the positions shown so that pins or plugs in the first intermatable electrical connector 70 engage a corresponding set of plugs or pins in the second intermatable electrical connector 72 when the video camera unit 20 and the surgical lighthead 14 are moved together relative to one another. The intermatable electrical connectors 70, 72 send power and command signals to the camera unit and return video signals for use by the control unit and the monitor to generate the display of the surgical procedure.

As noted above, a primary advantage of the subject surgical video system is the ability to provide full 360° video image rotation and beyond. The preferred embodiment of the modular digital video camera unit adapted to provide full 360° video image rotation is shown in detail in FIGS. 4–8. Turning now to those figures, the video camera 22 essentially comprises a single rectangular circuit board 80 having a lens system 82 on one end, a mechanical mounting area 84 on the other end, and a central electrical connector area 86 disposed therebetween. The electrical connector area provides electrical access to control electronics, power, and other functional circuits within the video camera 22. Preferably, in accordance with the present invention, the camera is a single chip advanced digital camera available from Sony having a resolution of at least 460 lines. Also, the preferred digital camera has a 12×zoom capability to meet the needs of most surgical videographic requirements. A wiring harness 90 interfaces the electrical connector area 86 of the circuit board 80 to the first intermatable connector 70 via an electromechanical commutator 92. The electrical commutator includes a set of internal precision slip rings to enable full 360° rotation of the circuit board 80 relative to the first intermatable electrical connector 70 as the camera is rotated in response to signals from the control unit 26. The top end of the commutator is freely rotatable relative to the bottom end.

Figure 7:
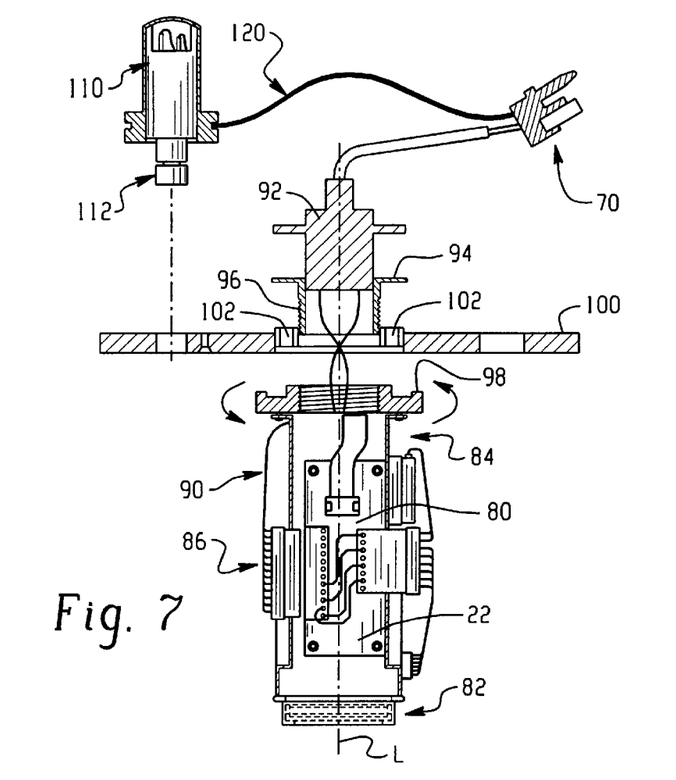
FIG. 7 is a partial exploded view of the modular digital video camera unit shown in FIG. 5.
Figure 8:
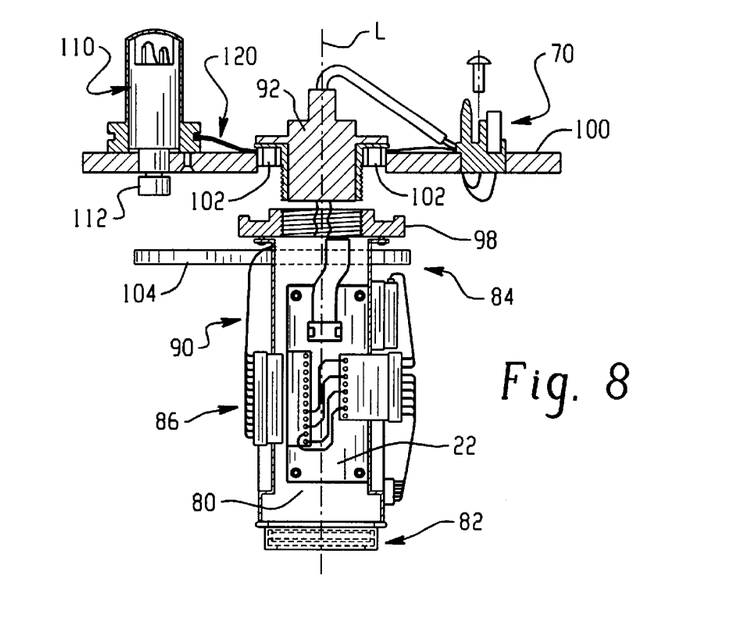
FIG. 8 shows a partially assembled view of the exploded modular digital video camera unit shown in FIG. 7.

As best shown in FIGS. 7 and 8, the commutator 92 is held in place in the base portion 60 by a mechanical slip ring flange 94. The slip ring flange has a top member 96 with external threads and a smooth internal passageway adapted to frictionally engage in a corresponding outer surface of the commutator. A bottom member 98 of the slip ring flange 94 has internal threads so that the top and bottom members 96, 98 can be securely fastened together on opposite sides of a rigid plate member 100 in a manner illustrated in FIGS. 5 and 6. During use of the subject modular digital video camera unit, the plate member 100 does not move relative to the surgical lighthead but, rather, remains fixed in position relative to the lighthead. The top and bottom flange members 96, 98 are carried on the plate member 100 by a press fit bearing member 102. In that way, the entire slip ring flange 94 is freely rotatable relative to the plate member 100.

The mechanical mounting area 84 of the circuit board 80 is fixedly attached to the bottom member 98 of the slip ring flange 94 as shown. In that way, the circuit board 80 moves together with the bottom member 98 of the slip ring flange. As shown best in FIGS. 4, 5, 7, and 8, a flexible belt member 104 is used to operatively connect a gear like portion of the bottom member 98 of the slip ring flange 94 to an electric drive motor 110. The electric motor includes a drive gear 112 that extends below the plate member 100 as shown. A body 114 of the gear motor is fixedly attached to the plate member 100 using suitable fasteners. In the preferred embodiment of the invention, the drive motor is used to rotate the bottom member 98 of the slip ring flange 94 to effect rotation of the entire circuit board 80 and lens system 82 carried thereon. In that way, a full 360° video image rotation and an unlimited number of multiple complete revolutions of the camera and image is realized.

The drive motor 110 includes a set of lead wires 120 for controlling rotational speed and direction of the motor. The lead wires 120 extend from the motor to the first intermatable electrical connector 70 as shown. Preferably, the drive motor lead wires are isolated from the various command signal and video image signal wires that extend from the circuit board 80 through the commutator 92 and into the first electrical connector 70.

In order to provide a reasonable measure of rigidity and vibrational energy immunity to the subject modular digital video camera unit, the lens end 82 of the circuit board 80 is rotatably connected to the outer housing 50 of the video camera unit using an annular flange 122 and bearing member 124. Preferably, the annular flange 122 is securely bolted or otherwise fastened to the lens end 82 of the circuit board 80. The outer end of the flange 122 is press fitted into the inner diameter of the lower bearing 124. The flange 122 rotates with the circuit board as it rotates. The bearing 124 enables smooth rotation of the lower end of the circuit board while simultaneously providing accurate alignment and locating of the lens along the axial center line L of the surgical lighthead throughout the full 360° camera rotation and throughout multiple complete rotations.

As noted above, the video signals originating from the modular digital video camera unit 20 are carried on digital video signal lines that extend from the lower surgical lighthead unit 14 to the control unit 26 and in turn to the video monitor 24 and then selectively to the recorder unit 42. The digital video signal lines 130 are illustrated generally in FIG. 1. Overall, the signal lines extend through a hub member 132 of the support system 16 and downward through the multiple articulated arm segments of the lower surgical lighthead unit 14.

In accordance with the present invention, the digital video signal lines 130 are cabled separately from the set of electrical power supply lines 134 used to deliver electrical energy to the surgical lightheads. In addition, the digital video signal lines are held in a spaced apart relationship relative to the power supply lines so that noise on the video signal lines is minimized.

Figure 9:
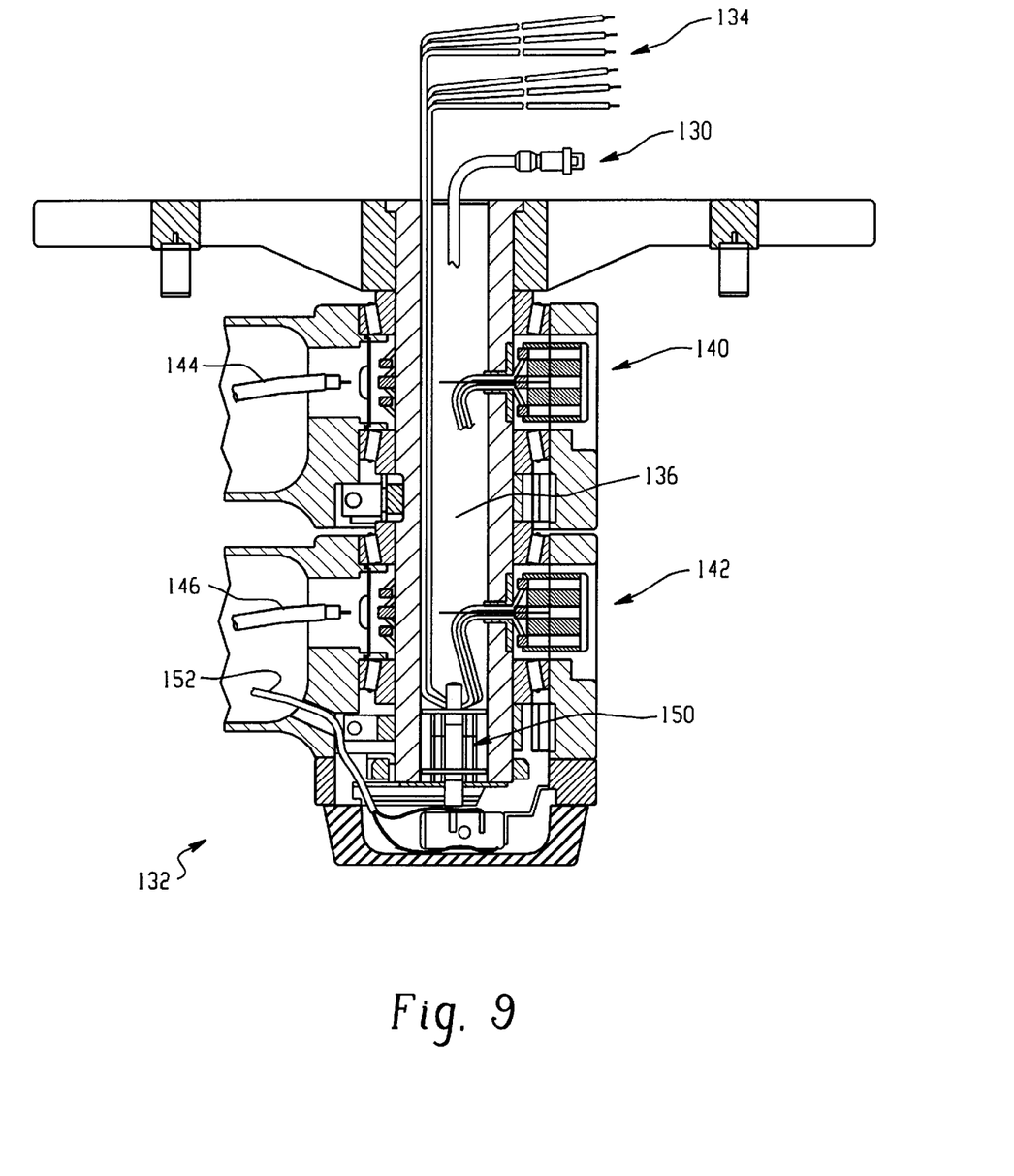
FIG. 9 is a cross-sectional view of a support system member showing the power and signal wire routing of the invention taken along line 9—9 of FIG. 1.
Figure 10:
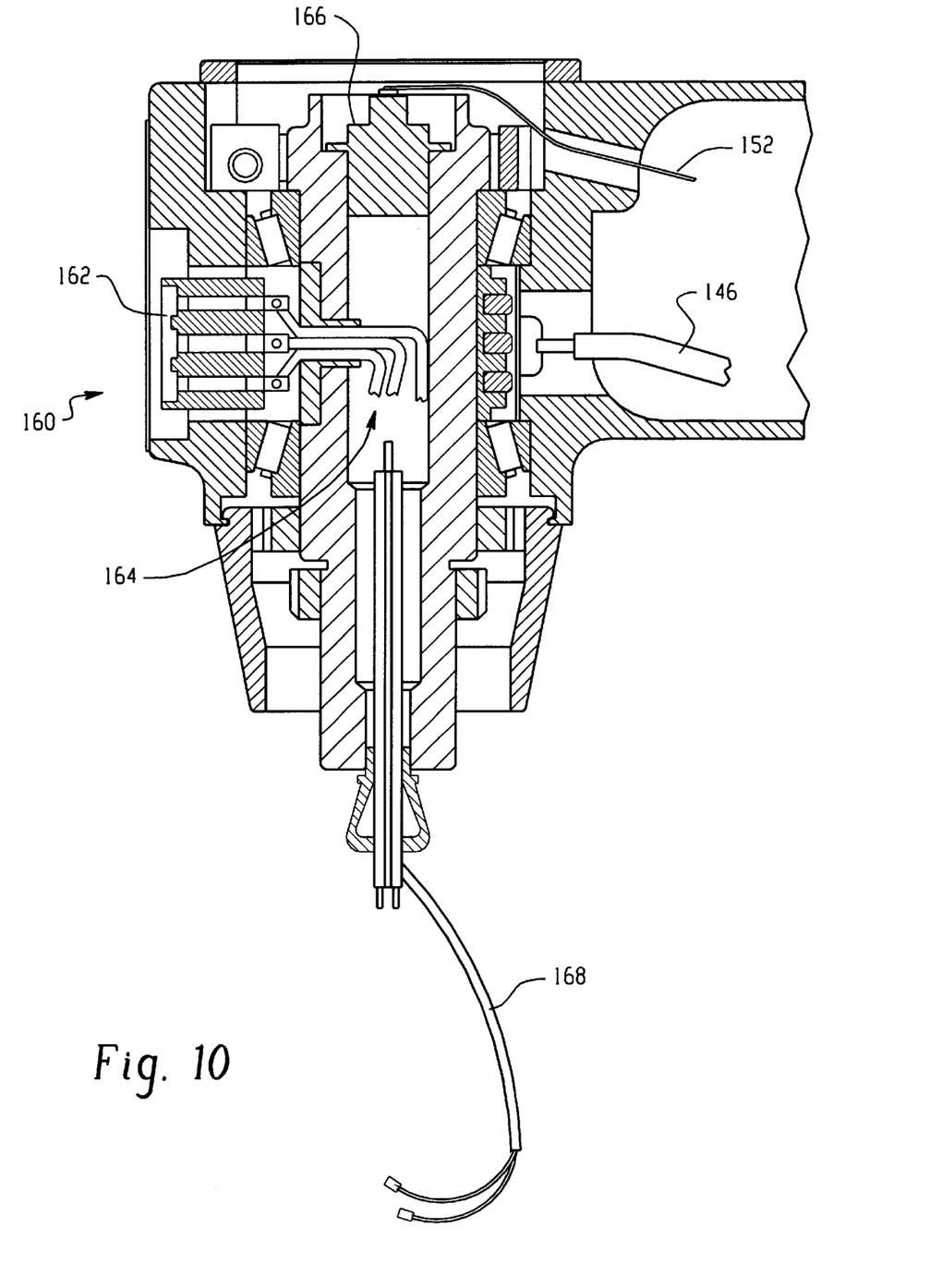
FIG. 10 is a cross-sectional view of an intermediate support system member showing the power and signal wire routing of the invention taken along line 10—10 of FIG. 1; and, FIG. 11 is a plan illustration showing the lower arm portion of the support system and the lower lighthead in partial breakaway view taken along line 11—11 of FIG. 1.
Figure 11:
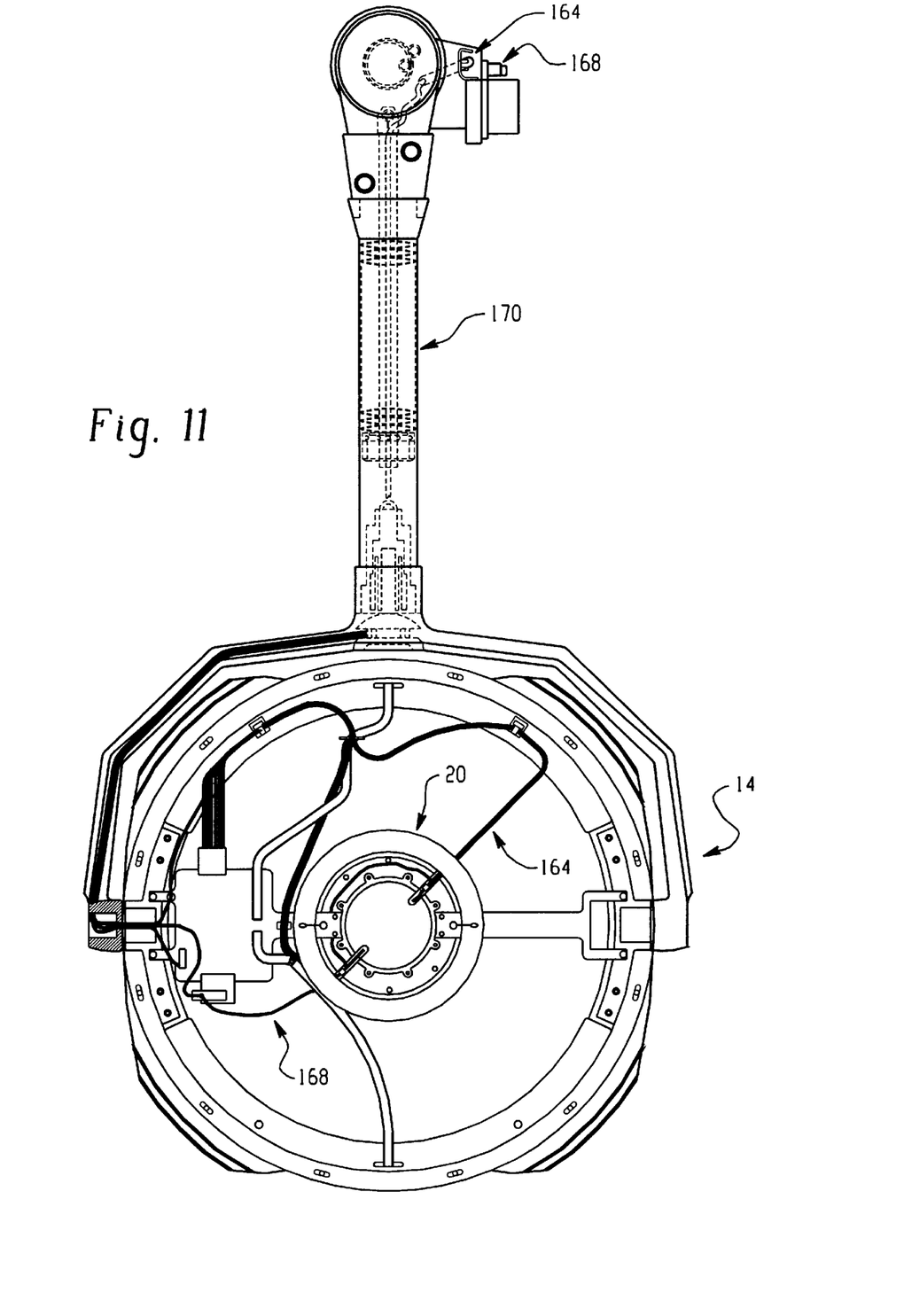

FIGS. 9–11 generally illustrate the manner in which the digital video signal lines 130 are carried through the lower surgical lighthead support members in a spaced apart relationship relative to the power supply lines 134. Turning first to FIG. 9, the hub member 132 defines a hollow passageway 136 adapted to receive the digital video signal lines 130 and a pair of top and bottom power supply lines 134. A pair of slip ring type commutators 140, 142 are provided to enable an electromechanical interface between the power supply lines 134 and first and second electric light power cables 144 and 146, respectively. The slip ring type commutators 140, 142 are disposed in a stacked relationship on the hub member 132 to enable the respective upper and lower support systems holding the surgical lightheads 12, 14 to be freely rotated through multiple revolutions without twisting the power supply lines 134.

Similar to the above, in order to prevent twisting of the digital video signal lines 130, a rotatable commutator unit 150 is disposed in the lower end of the hub member 132 as shown. The commutator unit 150 provides an electromechanical interface between the set of digital video signal lines 130 that extend through the ceiling and wall toward the control unit and a set of lower video signal lines 152 that extend downwardly from the hub unit toward the lower surgical lighthead 14. The rotatable commutator unit 150 is similar in form and function to the commutator unit 92 described above in connection with the modular digital video camera unit 20.

Turning now to FIG. 10, a pivot joint member 160 of the support system connected to the lower surgical lighthead 14 is illustrated in cross section. As shown there, an electric power slip ring commutator 162 is provided to enable a rotatable electromechanical interface between the second set of electric light power cables 146 and lower power cables 164 extending toward the lower surgical lighthead 14. In addition to the above, a rotatable commutator unit 166 is disposed in the pivot joint member 160 as shown to enable an electromechanical rotatable connection between the first set of lower video signal lines 152 and a second set of lower video signal lines 168. The lower power cables 164 and the second set of lower video signal lines 168 extend downwardly from the pivot joint member 160 toward the lower surgical lighthead 14 in a manner to be described below in connection with FIG. 11. Preferably, the rotatable commutator unit 166 in the pivot joint member has equivalent form and function to the commutator 92 described above in connection with the modular digital video camera unit 20.

Turning lastly to FIG. 11, the lower surgical lighthead 14 is shown together with a lower arm member 170 used to support the lighthead relative to the surgical field or region of interest. The second set of lower video signal lines 168 enter the lower arm member 170 on a first end thereof together with the lower power cables 164 as shown. The second set of lower video signal lines are routed through the lower arm member in a spaced apart relationship relative to the electric power cables. At the surgical lighthead 14, the second set of lower video signal lines 168 are routed radially inwardly in a first direction toward the modular digital video camera unit 20 as shown. The power cables 164 are also routed radially inwardly but are separated from the lower video signal lines to reduce the noise content in the video signals.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A surgical video system for capturing an image of a surgical procedure and displaying the image on a video monitor, the video system comprising:
    a surgical lighthead adapted to generate a light beam and direct the light beam towards a region of interest;
    a video camera integrated into the surgical lighthead for generating an image representative of a view of the region of interest, the video camera being adapted to physically rotate at least 360° relative to the surgical lighthead in response to a first command signal to thereby provide a rotated image representative of a rotated view of the region of interest;
    a commutator in said surgical lighthead for enabling said video camera to physically rotate at least said 360° relative to the surgical lighthead;
    a video monitor adapted to receive the input image and the rotated input image and display at least a one of the image of the region of interest and the rotated image of the region of interest in response to the input image and the rotated image, respectively; and,
    a control unit operatively connected to the video camera for generating said first command signal in response to an input signal from an operatively associated external source.

2. The surgical video system according to claim 1 wherein said video camera integrated into the at surgical lighthead is a digital video camera adapted to generate a digital image signal representative of the region of interest for display on the video monitor.

3. The surgical video system according to claim 2 further comprising a footswitch operatively connected to said control unit for selectively generating said input signal when the footswitch is in a first position, the control unit generating said first command signal in response to the input signal when the footswitch is in said first position to initiate relative rotational movement between the digital camera and the surgical lighthead.

4. The surgical video system according to claim 2 further comprising a manual keypad operatively connected to said control unit for selectively generating said input signal in response to manual contact of the manual keypad from a human operator, the control unit generating said first command signal in response to the input signal when the manual keypad is contacted by the human operator to initiate relative rotational movement between the digital camera and the surgical lighthead.

5. The surgical video system according to claim 2 further comprising a remote transmitter operatively connected to said control unit for selectively generating said input signal in response to manual contact of the remote transmitter from a human operator, the control unit generating said first command signal in response to the input signal when the remote transmitter is manually contacted by the human operator to initiate relative rotational movement between the digital camera and the surgical lighthead.

6. A surgical video system for capturing an image of a surgical procedure and displaying the image on a video monitor remote from the surgical procedure, the video system comprising:
    at least one surgical lighthead adapted to generate a light beam and direct the light beam towards a region of interest;
    a video camera integrated into the at least one surgical lighthead for generating an image of a view of the region or interest, the video camera being adapted to physically rotate an unlimited number of revolutions relative to the at least one surgical lighthead, to rotate the image in response to a first command signal to generate a rotated image representative of a rotated view of the region of interest;
    a video monitor adapted to receive the input image and the rotated input image and selectively display at least one of the image of the region of interest and the rotated image of the region of interest in response to the input image signal and the rotated image signal, respectively;
    a control unit operatively connected to the video camera for generating said first command signal in response to an input signal from an operatively associated external source;
    a rotatable frame supported within said at least one surgical lighthead, the rotatable frame carrying the video camera on the at least one surgical lighthead;
    an electric drive motor disposed within the at least one surgical lighthead and operatively drivingly connected with the rotatable frame, the electric drive motor being adapted to selectively rotate the rotatable frame and the video camera carried thereon in response to said first command signal;
    an electric slip ring connector for electromechanically connecting video signal lines from said video camera to second video signal lines extending through said at least one surgical lighthead to said control unit;
    a first plug connector for connecting first power lines extending from said electric drive motor to second electric power lines extending from the at least one surgical lighthead to the control unit; and,
    a second plug connector for connecting first electric video lines extending from the slip ring connector to second electric video lines extending from the at least one surgical lighthead to the control unit.

7. The surgical video system according to claim 6 wherein said rotatable frame, said electric drive motor, said digital video camera, said slip ring connector, said first plug connector, and said second plug connector collectively form a modular digital video camera unit that is selectively removable from the at least one surgical lighthead and selectively replaceable with a second modular digital video camera unit.

8. The surgical video system according to claim 6 wherein:
    said at least one surgical lighthead is carried on an articulated support arm;
    the articulated support arm is adapted to carry power supply lines from an associated source of lighting power to the at least one lighthead; and,
    the articulated support arm is adapted to carry said second electric video lines front said video camera in the at least one lighthead to the control unit separated from the power supply lines.

9. The surgical video system according to claim 8 wherein:
    said power supply lines include at least one first slip ring connector for rotatably connecting said at least one surgical lighthead to an operatively associated source or electric power; and, said second digital video signal lines carried by said articulated support arm include at least one second slip ring connector for rotatably connecting said video camera to the control unit.

10. The surgical system according to claim 9 wherein:

said power supply lines include a plurality of first slip ring connectors rotatably connecting the at least one surgical lighthead to the operatively associated source of electric power; and, said second digital video signal line carried by the articulated support arm includes a plurality of second slip ring connectors rotatably connecting the video camera to the control unit.

11. A surgical video system for use with surgical lighting equipment to capture an image of a surgical procedure performed in a region of interest, the video system comprising:

at least one surgical lighthead adapted to generate a light beam and direct the light beam towards the region of interest, the lighthead including a handle with a housing for manually manipulating the lighthead;

a video camera within the handle housing of the surgical lighthead for generating an image of a view of the region of interest, the video camera being adapted to selectively rotate the image relative to the at least one surgical lighthead by selective rotation of the camera through at least one full revolution relative to the handle housing in response to a first command signal to generate a modified image representative of a modified view of the region of interest;

a control unit operatively connected to the video camera for generating said command signal in response to an input signal from an operatively associated external source; and means for carrying control, power and video signals to and from the camera, thereby allowing the video camera to rotate at least one full revolution relative to the at least one surgical lighthead, the means including:
 a commutator for connecting first electrical lines from the video camera to second electrical lines; and
 a connector for connecting the second electrical lines extending from the commutator to third electrical lines extending through the at least one surgical lighthead to the control unit.

12. A surgical video system for use with surgical lighting equipment to capture an image of a surgical procedure performed in a region of interest, the video system comprising:

at least one surgical lighthead adapted to generate a light beam and direct the light beam towards the region of interest;

a video camera integrated into the at least one surgical lighthead for generating an image representative of a view of the region of interest, the video camera being adapted to selectively modify the image in response to a first command signal by physically rotating relative to at least one surgical lighthead at least 360° in response to said first command signal to rotate said digital image representative of the region of interest;

a control unit operatively connected to the video camera for generating said command signal in response to an input signal from an operatively associated external source;

an electric drive motor operatively connected with the control unit and the video camera and disposed within the at least one surgical lighthead; and means operative to carry control and video signals to and from the camera, respectively, thereby allowing the video camera to rotate an unlimited number of turns relative to said at least one surgical lighthead, the means including:
 a slip ring commutator for connecting first video and control lines from the video camera to second video and control lines; and
 a first connector adapted to mate with a second connector disposed in the at least one surgical lighthead, wherein the first and second connectors connect first power lines extending from the electric drive motor to second power lines extending through the at least one surgical lighthead to the control unit, and the second video and control lines extending from the slip ring commutator to third video and control lines extending through the at least one surgical lighthead to the control unit.

13. The surgical video system according to claim 11 further comprising a footswitch operatively connected to said control unit for selectively generating said input signal exclusively when the footswitch is in a first position, the control unit generating said first command signal in response to the input signal when the footswitch is in said first position to initiate relative rotational movement between the digital camera and the at least one surgical lighthead.

14. The surgical video system according to claim 11 further comprising a manual keypad operatively connected to said control unit for selectively generating said input signal in response to manual contact of the manual keypad from a human operator, the control unit generating said first command signal in response to the input signal when the manual keypad is contacted by the human operator to initiate relative rotational movement between the digital camera and the at least one surgical lighthead.

15. The surgical video system according to claim 11 further comprising a remote transmitter operatively connected to said control unit for selectively generating said input signal in response to manual contact of the remote transmitter from a human operator, the control unit generating said first command signal in response to the input signal when the remote transmitter is manually contacted by the human operator to initiate relative rotational movement between the digital camera and the at least one surgical lighthead.

16. The surgical video system according to claim 11 wherein said digital video camera is adapted to form a modular digital video camera unit that is selectively removable from the at least one surgical lighthead and selectively replaceable with a second modular digital video camera unit.

17. A surgical video system for use with surgical lighting equipment to capture an image of a surgical procedure performed in a region of interest, the video system comprising:

at least one surgical lighthead adapted to generate a light beam and direct the light beam towards the region of interest;

a video camera adapted to generate an image representative of a view of the region of interest, the video camera being adapted to selectively modify the image in response to a first command signal, through motor driven rotation up to 360° in order to rotate said image representative of the view of the region of interest, in response to a second command signal, by altering the magnification of said image representative of the view of the region of interest, and, in response to a third command signal, by altering the focus of said image representative of the view of the region of interest;

a control unit operatively connected to the video camera for generating said command signal in response to an input signal from an operatively associated external source; and an electromechanical apparatus to allow rotating the video camera beyond a single revolution in relation to the at least one lighthead by electromechanically engaging power and video lines extending from the video camera through the at least one lighthead to the control unit by a use of slip ring commutators, wherein the video camera, the motor and the electromechanical apparatus form a removable replaceable modular video camera unit integrated into the at least one surgical lighthead.

18. In combination:

a surgical lighthead; and a modular video system integrated into the surgical lighthead, the modular video system including:
  a motor
  a drive mechanism
  a video camera, the video camera being connected to the motor through the drive mechanism so as to be rotatable relative to the surgical lighthead through at least one full rotation, about an axis perpendicular to a lens of the camera, in response to an electronic signal received by the motor, from an operatively associated source; and means for carrying control, power and video signals to and from the camera and allowing the video camera to rotate through at least one full rotation, the means including:
  a slip ring commutator for connecting first video/control/power lines from the video camera to second video/control/power lines; and
  a connector disposed about the video camera for connecting first power lines extending from the motor to second power lines extending through the at least one surgical lighthead to the control unit, and
  the second video/control/power lines extending from the slip ring commutator to third video/control/power lines extending through the at least one surgical lighthead to the control unit.

19. A removable modular surgical video system integrated into a surgical lighthead to record an image of a surgical procedure in response to a signal from a control unit and display the image on a video monitor, the video system including:

a video camera adapted to generate an image of a view of a region of interest, the video camera being physically rotatable at least 360° relative to the surgical lighthead;

a drive system including a motor operatively connected with the video camera to rotate the camera relative to the surgical lighthead a selective number of revolutions; and an electromechanical device to allow the physical rotation of the camera of at least 360° relative to the surgical lighthead.

20. A removable replaceable, modular surgical video system according to claim 19, wherein the electromechanical device includes:

an electric slip ring commutator for connecting first video, signal and power lines from the video camera to second video, signal and power lines extending into the surgical lighthead;

a first plug connector for connecting first motor power lines extending from the motor to second power motor lines extending through the surgical lighthead to the control unit; and, a second plug connector for connecting the second video, control and power lines extending from the slip ring commutator to third video, control and power lines extending through the surgical lighthead to the control unit.

* * * * *